US012676240B1

(12) United States Patent
Alexander et al.

(10) Patent No.: US 12,676,240 B1
(45) Date of Patent: Jul. 7, 2026

(54) ANESTHESIA PRE-SCREENING SYSTEM AND DIGITAL ANESTHESIA PRE-SCREENING PROCESSES

(71) Applicants: Tina Alexander, Sugar Land, TX (US); Danny Mathew Joseph, Sugar Land, TX (US)

(72) Inventors: Tina Alexander, Sugar Land, TX (US); Danny Mathew Joseph, Sugar Land, TX (US)

(73) Assignee: ASK MEDICAL LLC, Sugar Land, TX (US)

( * ) Notice: Subject to any disclaimer, the term of this patent is extended or adjusted under 35 U.S.C. 154(b) by 0 days.

(21) Appl. No.: 19/007,366

(22) Filed: Dec. 31, 2024

Related U.S. Application Data

(60) Provisional application No. 63/616,831, filed on Jan. 2, 2024.

(51) Int. Cl.
G16H 50/30 (2018.01)
G16H 10/20 (2018.01)
G16H 10/60 (2018.01)

(52) U.S. Cl.
CPC ............. G16H 50/30 (2018.01); G16H 10/20 (2018.01); G16H 10/60 (2018.01)

(58) Field of Classification Search
CPC ......... G16H 50/30; G16H 10/20; G16H 10/60
See application file for complete search history.

(56) References Cited

U.S. PATENT DOCUMENTS

2023/0245779 A1 *  8/2023  Moussali ............... G16H 10/60
                                                           705/3

FOREIGN PATENT DOCUMENTS

CN        102651098 B   *  3/2016

OTHER PUBLICATIONS

Almeshari M, Khalifa M, El-Metwally A, Househ M, Alanazi A. Quality and accuracy of electronic pre-anesthesia evaluation forms. Comput Methods Programs Biomed. Jul. 2018; 160:51-56. doi: 10.1016/j.cmpb.2018.03.006. Epub Mar. 15, 2018. PMID: 29728246 (Year: 2018).*

* cited by examiner

*Primary Examiner* — Linh Giang Le
(74) *Attorney, Agent, or Firm* — Plager Schack LLP; Mark H. Plager; Stephen Hallberg

(57) ABSTRACT

An anesthesia pre-screening system and digital anesthesia pre-screening processes ("anesthesia pre-screening system and processes") are disclosed. The anesthesia pre-screening system and processes are configured to automatically calculate surgical risks based on (i) data from digital questionnaires completed by patients in advance of surgery, (ii) image data comprising patient photos, and (iii) medical data including preoperative vitals data and data results of testing. The anesthesia pre-screening system and processes are configured to automatically obtain digital consent forms with digital signatures of patients. The anesthesia pre-screening system and processes are further configured to provide anesthesia discharge instructions after calculating surgical risks.

10 Claims, 4 Drawing Sheets

ANESTHESIA PRE-SCREENING SYSTEM AND DIGITAL ANESTHESIA PRE-SCREENING PROCESSES

CLAIM OF BENEFIT TO PRIOR APPLICATION

This application claims benefit to U.S. Provisional Patent Application 63/616,831, entitled "PRE-ANESTHESIA SCREENING SYSTEM AND SOFTWARE-IMPLE-MENTED PROCESS," filed Jan. 2, 2024. The U.S. Provisional Patent Application 63/616,831 is incorporated herein by reference.

BACKGROUND

Embodiments of the invention described in this specification relate generally to pre-anesthesia screening before surgery and before application of anesthesia, and more particularly, to an anesthesia pre-screening system and related digital anesthesia pre-screening processes.

Conventionally, pre-anesthesia screening and evaluation is cumbersome, repetitive and inefficient. For instance, none of the conventional pre-anesthesia screening and evaluation mechanisms are implemented as pre-anesthesia screening software. Instead, the conventional pre-anesthesia screening and evaluation mechanisms involve human workers. Consequently, the existing conventional pre-anesthesia screening and evaluation mechanisms are labor intensive and costly. Furthermore, patients may find the pre-anesthesia screening and evaluation process conducted by medical professionals to be bothersome, especially since patients are often understandably focused on getting through their procedures.

Therefore, what is needed is a way to perform pre-anesthesia screening and evaluation digitally and more efficiently with less cost.

BRIEF DESCRIPTION

A novel anesthesia pre-screening system and novel digital anesthesia pre-screening processes (collectively referred to as the "anesthesia pre-screening system and processes") are disclosed. In some embodiments, the anesthesia pre-screening system and processes are configured to automatically calculate surgical risks based on (i) data from digital questionnaires completed by patients in advance of surgery, (ii) image data comprising patient photos, and (iii) medical data comprising preoperative vitals data and data results of testing. In some embodiments, the anesthesia pre-screening system and processes are configured to automatically obtain digital consent forms signed (as digital signatures) by patients. In some embodiments, the anesthesia pre-screening system and processes are further configured to provide anesthesia discharge instructions after calculating surgical risks.

In some embodiments, the data from digital questionnaires completed by patients comprise digital text data input by the patients and captured by the anesthesia pre-screening system. In some embodiments, the data from digital questionnaires completed by patients comprises digital audio data vocalized by the patients and captured by a microphone of the anesthesia pre-screening system. In some embodiments, the data from digital questionnaires completed by patients comprises video data captured by a camera of the anesthesia pre-screening system. In some embodiments, the anesthesia pre-screening system comprises a video parser that is configured to extract digital audio data from the video data captured by the camera of the anesthesia pre-screening system. In some embodiments, the anesthesia pre-screening system comprises an audio-to-text system that is configured to process sound-waves of the digital audio data and output text data corresponding to the audio vocalized by the patients.

In some embodiments, the image data comprises patient photos captured by the camera of the anesthesia pre-screening system. In some embodiments, the camera is an embedded camera of a computing device comprising one of a mobile device, a tablet computing device, a computer, and a laptop computer. In some embodiments, the camera is an external camera that is communicably connected to the anesthesia pre-screening system.

In some embodiments, the medical data comprises preoperative vitals data captured by a digital medical device of the anesthesia pre-screening system that is applied to a patient before anesthesia. In some embodiments, the medical data comprises data results of testing one or more biological or bodily samples of a patient before anesthesia.

In some embodiments, the digital anesthesia pre-screening processes comprise a high-level digital anesthesia pre-screening process and a detailed digital anesthesia pre-screening process. In some embodiments, the high-level digital anesthesia pre-screening process comprises (i) receiving contact information of a patient ("patient contact information"), (ii) transmitting, to an account of the patient, a hyperlink address to a pre-screening questionnaire service that is configured to provide a pre-screening questionnaire with a plurality of questions for the patient to answer, (iii) visually outputting a consent signature field on the pre-screening questionnaire after the plurality of questions are answered, (iv) receiving either a denial of consent or an acceptance of content by a digital signature of the patient in the consent signature field ("digital patient consent signature"), (v) automatically incorporating, in a patient history data structure, the digital patient consent signature and the answers to the plurality of questions of the pre-screening questionnaire, and (vi) presenting a plurality of pre-anesthesia indicators comprising a recommendation of lab work to complete before surgery, medical clearances required before surgery, and medications to stop in advance of surgery.

In some embodiments, the received patient contact information is input, before anesthesia, by an authorized member of a pre-screening team comprising a plurality of pre-screening members.

In some embodiments, the pre-screening questionnaire service visually outputs a pre-screening questionnaire website that provides a patient-facing user interface on a front-end server of the anesthesia pre-screening system. In some embodiments, the pre-screening questionnaire service comprises a cloud application service ("pre-anesthesia screening cloud application service") that is hosted by a cloud-based anesthesia pre-screening server of the anesthesia pre-screening system.

In some embodiments, the patient history data is pre-completed by a pre-screening member of the pre-screening team. In some embodiments, the patient history data comprises a type of surgery, individual department guidelines, and specific patient history data for a particular patient. In some embodiments, the patient history data further comprises relevant pathology data with respect to the particular patient.

In some embodiments, the patient history data structure is configured to store the digital patient consent signature and the answers to the plurality of questions of the pre-screening questionnaire as patient pre-screening data that augments patient history data. In some embodiments, the patient history data structure is organized to optimize, by the anesthesia pre-screening system, storage and utilization of the patient pre-screening data and the patient history data.

In some embodiments, the digital anesthesia pre-screening processes involve one or more software implementation(s) configured to run on a computing device of the anesthesia pre-screening system. In at least one embodiment, the digital anesthesia pre-screening processes are implemented as a software as a service (SaaS). In some embodiments, the SaaS implementation of the digital anesthesia pre-screening processes provide a pre-screening questionnaire cloud application service. In some embodiments, the pre-screening questionnaire cloud application service is configured to automatically obtain digital consent forms signed by patients via digital signatures. In some embodiments, the pre-screening questionnaire cloud application service is configured to provide anesthesia discharge instructions.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

Figure 1:
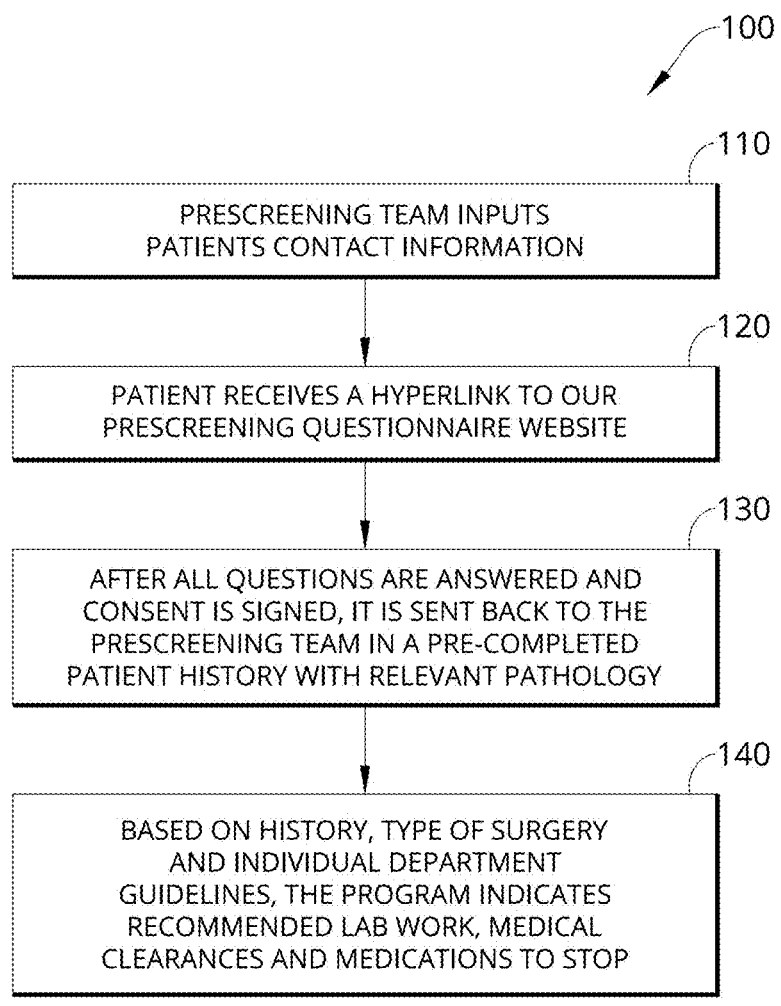
FIG. 1 conceptually illustrates a high-level pre-anesthesia screening process in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Embodiments of the invention described in this Specification include an anesthesia pre-screening system and digital anesthesia pre-screening processes. In some embodiments, the anesthesia pre-screening system and processes are configured to automatically calculate surgical risks based on (i) data from digital questionnaires completed by patients in advance of surgery, (ii) image data comprising patient photos, and (iii) medical data comprising preoperative vitals data and data results of testing.

In some embodiments, the data from digital questionnaires completed by patients comprise digital text data input by the patients and captured by the anesthesia pre-screening system. In some embodiments, the data from digital questionnaires completed by patients comprises digital audio data vocalized by the patients and captured by a microphone of the anesthesia pre-screening system. In some embodiments, the data from digital questionnaires completed by patients comprises video data captured by a camera of the anesthesia pre-screening system. In some embodiments, the anesthesia pre-screening system comprises a video parser that is configured to extract digital audio data from the video data captured by the camera of the anesthesia pre-screening system. In some embodiments, the anesthesia pre-screening system comprises an audio-to-text system that is configured to process sound-waves (also referred to as "waveform signals", "wave-forms", etc.) of the digital audio data and output text data corresponding to the audio vocalized by the patients.

In some embodiments, the image data comprises patient photos captured by the camera of the anesthesia pre-screening system. In some embodiments, the camera is an embedded camera of a computing device comprising one of a mobile device, a tablet computing device, a computer, and a laptop computer. In some embodiments, the camera is an external camera that is communicably connected to the anesthesia pre-screening system.

In some embodiments, the medical data comprises preoperative vitals data captured by a digital medical device of the anesthesia pre-screening system that is applied to a patient before anesthesia. In some embodiments, the medical data comprises data results of testing one or more biological or bodily samples of a patient before anesthesia.

In some embodiments, the digital anesthesia pre-screening processes comprise a high-level digital anesthesia pre-screening process and a detailed digital anesthesia pre-screening process. In some embodiments, the high-level digital anesthesia pre-screening process comprises (i) receiving patient contact information, (ii) transmitting, to an account of the patient, a hyperlink address to a pre-screening questionnaire service that is configured to provide a pre-screening questionnaire with a plurality of questions for the patient to answer, (iii) visually outputting a consent signature field on the pre-screening questionnaire after the plurality of questions are answered, (iv) receiving either a denial of consent or an acceptance of content by a digital signature of the patient in the consent signature field ("digital patient consent signature"), (v) automatically incorporating, in a patient history data structure, the digital patient consent signature and the answers to the plurality of questions of the pre-screening questionnaire, and (vi) presenting a plurality of pre-anesthesia indicators comprising a recommendation of lab work to complete before surgery, medical clearances required before surgery, and medications to stop in advance of surgery.

In some embodiments, the received patient contact information is input, before anesthesia, by an authorized member of a pre-screening team comprising a plurality of pre-screening members.

In some embodiments, the pre-screening questionnaire service visually outputs a pre-screening questionnaire website that provides a patient-facing user interface on a front-end server of the anesthesia pre-screening system. In some embodiments, the pre-screening questionnaire service comprises a pre-screening questionnaire cloud application service that is hosted by a cloud-based anesthesia pre-screening server of the anesthesia pre-screening system.

In some embodiments, the patient history data is pre-completed by a pre-screening member of the pre-screening team. In some embodiments, the patient history data comprises a type of surgery, individual department guidelines, and specific patient history data for a particular patient. In some embodiments, the patient history data further comprises relevant pathology data with respect to the particular patient.

In some embodiments, the patient history data structure is configured to store the digital patient consent signature and the answers to the plurality of questions of the pre-screening questionnaire as patient pre-screening data that augments patient history data. In some embodiments, the patient history data structure is organized to optimize, by the anesthesia pre-screening system, storage and utilization of the patient pre-screening data and the patient history data.

In some embodiments, the digital anesthesia pre-screening processes involve one or more software implementation(s) configured to run on a computing device of the anesthesia pre-screening system. In at least one embodiment, the digital anesthesia pre-screening processes are implemented as a software as a service (SaaS). In some embodiments, the SaaS implementation of the digital anesthesia pre-screening processes provide a pre-screening questionnaire cloud application service. In some embodiments, the pre-screening questionnaire cloud application service is configured to automatically obtain digital consent forms signed by patients via digital signatures. In some embodiments, the pre-screening questionnaire cloud application service is configured to provide anesthesia discharge instructions.

As stated above, pre-anesthesia screening and evaluation is cumbersome, repetitive, and inefficient. For instance, none of the conventional pre-anesthesia screening and evaluation mechanisms are implemented as pre-anesthesia screening software. Instead, the conventional pre-anesthesia screening and evaluation mechanisms involve human workers. Consequently, the existing conventional pre-anesthesia screening and evaluation mechanisms are labor intensive and costly. Furthermore, patients may find the pre-anesthesia screening and evaluation process conducted by medical professionals to be bothersome, especially since patients are often understandably focused on getting through their procedures. Embodiments of the anesthesia pre-screening system and processes described in this specification solve such problems by a combination of hardware systems and software-implemented programs (some interactive and some automated) that expedite pre-screening, limits unnecessary phone calls/visits, etc., in advance of anesthesia for surgical procedures. Furthermore, the information obtained in advance of surgery is stored and utilized by the anesthesia pre-screening system in key data structures organized to optimize runtime processing of the software-implemented programs by the hardware systems, which include servers (such as cloud-based servers, virtual servers, etc.) with processing units, computers with CPUs, graphical processing units (GPUs), tensor processing units (TPUs), and other such computing devices and hardware resources.

Embodiments of the anesthesia pre-screening system and processes described in this specification differ from and improve upon currently existing options. In particular, there is no other pre-anesthesia screening system, software, program, or other automated system that can capture all needed information in advance of surgery with minimal hassle. Typically, the existing options include various hand-provided input on paper, by multiple different personnel speaking with a patient or systems that send out multiple different forms, questions, and various pre-anesthesia requirements to patients. While the conventional pre-anesthesia screening methods require medical personnel, which raises the overall costs involved, the other problem is that each patient is inundated with requirements and requests for information that are dispersed in time and through different channels-both digital and in-person. Furthermore, the conventional pre-anesthesia screening methods are bothersome to patients. By contrast, the anesthesia pre-screening system and processes of the present disclosure provides a digital/electronic solution that takes patients through all the anesthesia screening questions in questionnaire format, obtains digital signatures as required, complies with all applicable rules and regulations (e.g., HIPAA, HL7, etc.), is more efficient and less error-prone than human workers, and ends up being cheaper and faster for all involved.

The anesthesia pre-screening system and processes of the present disclosure may be comprised of the following elements. This list of possible constituent elements is intended to be exemplary only and it is not intended that this list be used to limit the anesthesia pre-screening system and processes of the present application to just these elements. Persons having ordinary skill in the art relevant to the present disclosure may understand there to be equivalent elements that may be substituted within the present disclosure without changing the essential function or operation of the anesthesia pre-screening system and processes.

1. A HIPAA compliant program that contacts/emails/texts patients with a link to a pre-anesthesia questionnaire
2. The questionnaire would accumulate the patient's medical history (based on patient input or by analyzing medical records)
3. Based on each anesthesia department guidelines (customizable for each user), the software lists recommended lab work, pre-screening testing, medical clearances required and which medications to stop
4. The questionnaire responses and recommendations are sent back to the Anesthesia department or user for review and subsequent modification
5. This program would have HL7 capability to analyze and input information from electronic health databases (Cerner, EPIC, etc.)
6. Program will automatically calculate surgical risks (American College of Surgeon's NSQIP Surgical Risk Calculator, Revised Goldman Cardiac Risk, Peri-operative Risk for Acute Kidney Injury, MELD, APACHE, etc.)
7. This program would include consent forms with digital signature
8. This program would incorporate patient photos (teeth, Mallampati, etc.), automatically include preoperative vitals and results of testing
9. This program would include anesthesia discharge instructions The various elements of the anesthesia pre-screening system and processes of the present disclosure may be related in the following exemplary fashion. It is not intended to limit the scope or nature of the relationships between the various elements and the following examples are presented as illustrative examples only.

The anesthesia pre-screening system and processes of the present disclosure generally works by a computer program that asks patients questions about their medical history (or inputs directly from a medical database). Based on each anesthesia department guidelines (customizable for each user), the software lists recommended lab work, pre-screening testing, medical clearances required and which medications to stop. This data is sent back to the Anesthesia department or User for review. Subsequent surgical risks can be calculated based on lab results and functional status. The Patient can digitally view and sign consent forms. The patient can upload photos of teeth, mallampati view with a digital camera. Anesthesia discharge instructions can be viewed prior to surgery.

To make the anesthesia pre-screening system and processes of the present disclosure, a person would write code for computer software that enables emails/texts with a link to pre anesthesia medical history questionnaire with photo capture/digital signature capabilities. The software would be HIPAA compliant and HL7 capable to input medical information from electronic health records (which provides the ability for the program to receive a patient's medical history and subsequently determine further evaluation and testing).

To use the anesthesia pre-screening system and processes of the present disclosure, a patient's email or cell is input by medical personnel into a website that runs this software. Website sends questionnaire results back to initial user.

By way of example, FIG. 1 conceptually illustrates a high-level pre-anesthesia screening process 100. The high-level pre-anesthesia screening process 100 is performed prior to anesthesia and surgery for a patient. As shown in this figure, the high-level pre-anesthesia screening process 100 starts with a pre-screening team inputting patient contact information (at 110). The patient's contact information includes, without limitation, email address, phone number, social media account names and addresses, other contact information (relatives, friends, designated care members, etc.).

Next, the high-level pre-anesthesia screening process 100 proceeds to a step at which the patient receives a hyperlink to a pre-screening questionnaire website (at 120). The pre-screening questionnaire website may be provided by a pre-anesthesia screening cloud application service hosted on a cloud-based anesthesia pre-screening server and accessible to the patient and other users through a front-end server. An example of a pre-anesthesia screening cloud application service hosted on a cloud-based anesthesia pre-screening server is described below, by reference to FIG. 3.

After all the questions in the pre-screening questionnaire are answered (by the patient) and after the patient has digitally signed the consent form, the high-level pre-anesthesia screening process 100 proceeds to a step at which the pre-screening questionnaire is automatically sent back to the pre-screening team with the patient's answers and signature included (at 130). In particular, sending back the patient's answers and signature involve transmitting data representations of the answers and signature in a patient history data structure form that is configured to automatically input the patient's answers and signature in a pre-completed history of the patient with relevant pathology information. The pre-completed history of the patient would have been partially completed by a member of the pre-screening team in advance.

Next, the high-level pre-anesthesia screening process 100 proceeds to recommend lab work, medical clearances, and medications to stop in advance of surgery (at 140) based on the history of the patient, the type of surgery that will be performed for the patient, and individual departmental guidelines and procedures. In some embodiments, surgical risks are calculated before, during, or after performance of the step for indicating recommendations for lab work, medical clearances, and medication stoppages. In some embodiments, the final step of the high-level pre-anesthesia screening process 100 may also include generating and providing post-surgery information including, without limitation, anesthesia discharge instructions.

Figure 2:
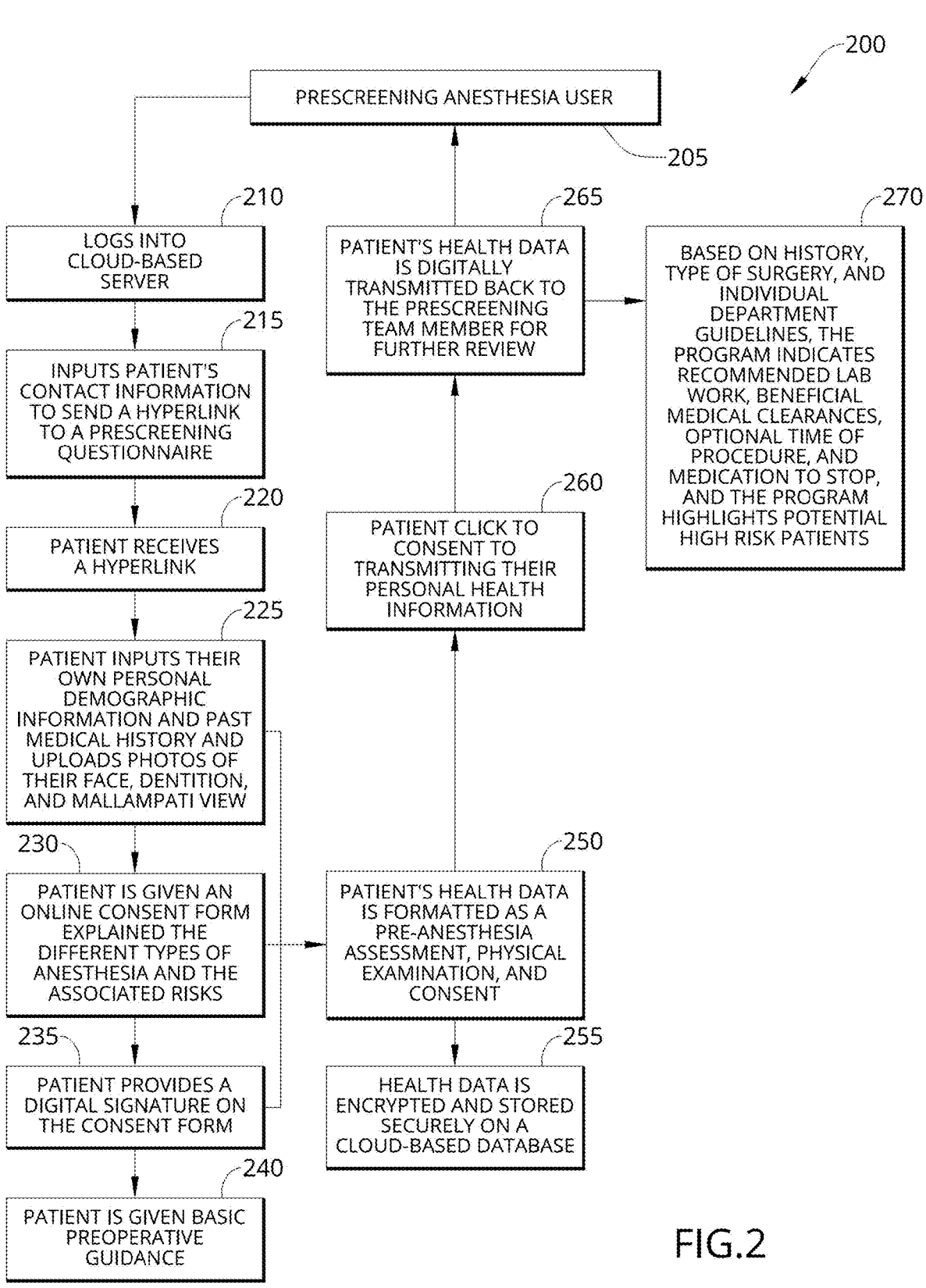
FIG. 2 conceptually illustrates a detailed pre-anesthesia screening process in some embodiments.

Turning now to another digital anesthesia pre-screening process, FIG. 2 conceptually illustrates the detailed pre-anesthesia screening process 200. As shown in this figure, the detailed pre-anesthesia screening process 200 is an interactive process involving a member of the pre-screening team who engages with an anesthesia user (or "patient") to perform a pre-screening evaluation in advance of surgery and before anesthesia is applied to the patient. Thus, the detailed pre-anesthesia screening process 200 starts when the member of the pre-screening team starts pre-screening the patient (at 205).

The detailed pre-anesthesia screening process 200 includes a step at which the pre-screening team member uses a computing device to access a website of the anesthesia pre-screening system by connection over a network to the front-end server. Once connected, the website presents user login fields which enable the pre-screening team member to log into the cloud-based pre-anesthesia screening cloud application service hosted by the cloud-based anesthesia pre-screening server (at 210). In some embodiments, the cloud-based pre-anesthesia screening cloud application service performs user authentication to ensure that the pre-screening team member is authorized to start the pre-screening process of the anesthesia user. The pre-screening team member is authenticated by validating user credentials provided by the member in the login fields on the website.

After the pre-screening team member is validly authenticated and is logged into the cloud-based server (at 210), the detailed pre-anesthesia screening process 200 proceeds to a step at which the pre-screening team member inputs the patient's contact information (at 215), which is used to send, to the patient, a hyperlink to a pre-screening questionnaire (at 215). After the patient receives the hyplerlink (at 220), the patient can interact with the pre-screening questionnaire to input or provide key information, data, and/or imagery (at 225). The key information, data, and imagery input by the patient would include the patient's own personal demographic information, past medical history data, and multiple image uploads comprising at least photos of the patient's face, dentition, and mallampati views (at 225).

Next, the detailed pre-anesthesia screening process 200 proceeds to a step at which the patient is presented with an online consent form (at 230) which includes information explaining different types of anesthesia and associated risks of each type of anesthesia (at 230). Once the patient reviews the online consent form with the relevant anesthesia type and risk information (at 230), the detailed pre-anesthesia screening process 200 moves forward to a step at which the patient provides his or her digital signature on the consent form (at 235). Then the detailed pre-anesthesia screening process 200 provides pre-operative guidance to the patient (at 240).

Contemporaneously with receiving the patient's input for their own personal demographic information, past medical history data, and the images (at 225) and receiving the patient's digital signature (at 235), the detailed pre-anesthesia screening process 200 performs some automated, back-end steps. In particular, one of the automated, back-end steps of the detailed pre-anesthesia screening process 200 is for aggregating the relevant patient-provided information, data, signature, and imagery (collectively referred to as the "aggregated patient questionnaire answers and signature") and formats the aggregated patient questionnaire answers and signature as patient health data (at 250), which includes pre-anesthesia assessment, physical examination, and consent data. As the patient's health data is subject to privacy rules (such as rules of HIPAA), the detailed pre-anesthesia screening process 200 performs another automated, back-end step for encrypting and securely storing the patient health data in a cloud-based database or other data storage (at 255).

From the patient's perspective, performance of the automated, back-end steps is seamless, such that after the patient provides his or her own digital signature for consent (at 235) and after reviewing the preoperative guidance (at 240), the detailed pre-anesthesia screening process 200 transitions to a step at which the patient clicks to consent to transmission of the patient's own personal health information (at 260). Upon clicking the consent (or selecting the consent tool, icon, or other graphical element), the detailed pre-anesthesia screening process 200 proceeds to the next step for digitally transmitting (at 265) the patient's health data back to the pre-screening team member (at 205) who was validly authenticated for login to the cloud-based server (at 210). Furthermore, the detailed pre-anesthesia screening process 200 proceeds to a final step for providing indications of recommended lab work for the patient, beneficial and/or required medical clearances, estimated/optional time span of the surgery/procedure, medications to stop using before anesthesia and surgery, and ultimately, highlighting potential high risk patients (at 270) based on the patient history, the type of surgery, the type of anesthesia, and the individual department guidelines. Then the detailed pre-anesthesia screening process 200 ends.

Figure 3:
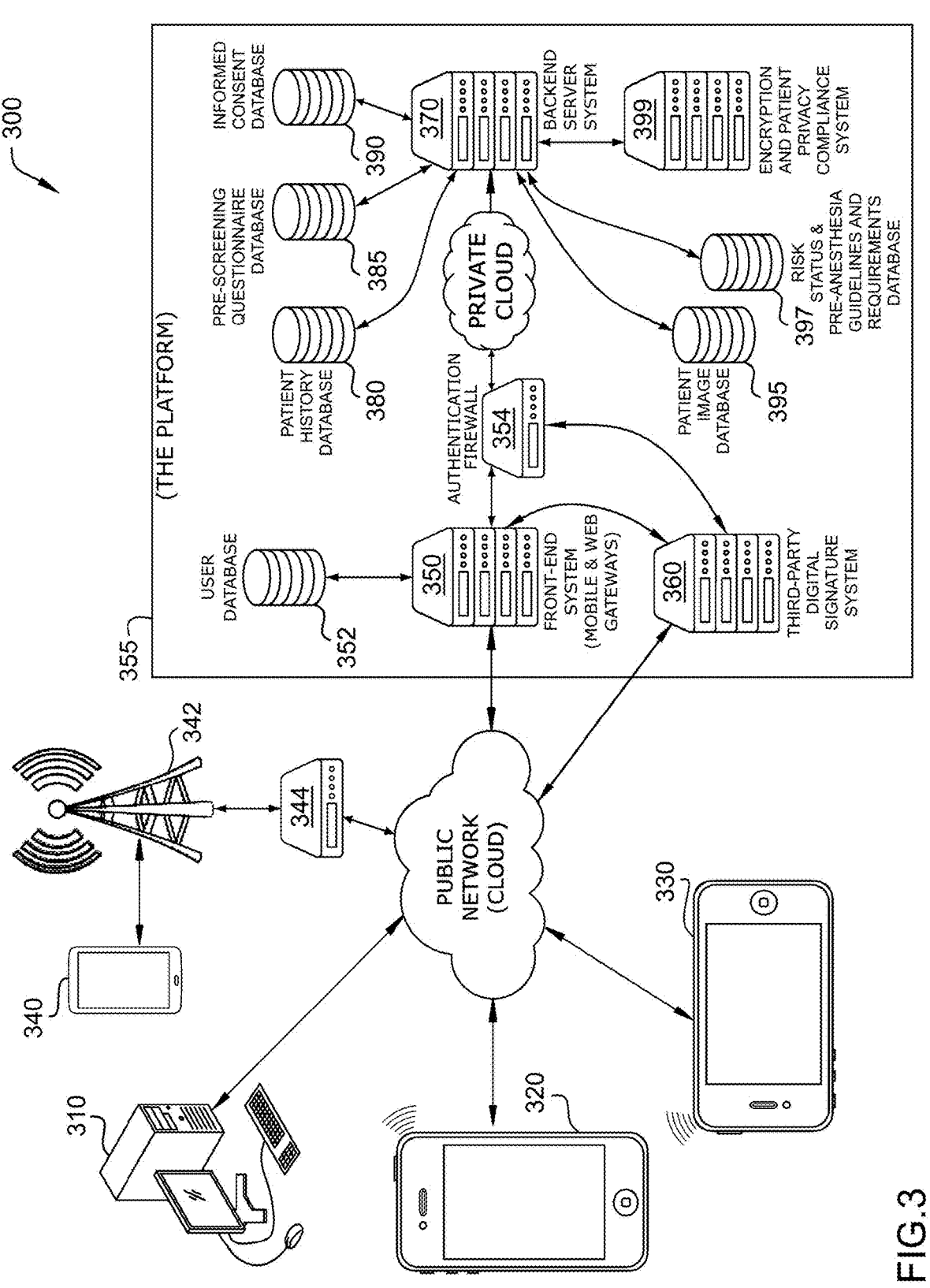
FIG. 3 conceptually illustrates a network architecture of a cloud-based anesthesia pre-screening system and platform that hosts a pre-screening questionnaire cloud application service in some embodiments.

By way of example, FIG. 3 conceptually illustrates a network architecture of a cloud-based pre-anesthesia screening system 300. As shown in this figure, the cloud-based pre-anesthesia screening system 300 provides a cloud-based platform 355 to which several client-side computing devices access the platform 355 over a network (such as the Internet, referred to in this figure as the "cloud"), which may involve wired connection or wireless connection (WiFi or cellular connection) over a wireless communication point 342 (e.g., a cell tower for cellular data communication) and by way of a gateway 344 to access the platform 355. The client-side computing devices shown in this figure include a desktop computer 310, a first mobile computing device 320, a second mobile computing device 330, and a tablet computing device 340. The client-side computing devices may be operable by patients or members of the pre-screening team.

Several systems, resources, and databases are incorporated into the platform 355 of the cloud-based pre-anesthesia screening system 300. Specifically, the cloud-based pre-anesthesia screening system 300 and platform 355 include a web/mobile front-end server 350 (which provides access to the website), a user database 352 (which stores relevant patient and team member information such as login credentials, contact information, etc.), an authentication firewall system 354 that prevents unauthorized access to backend services, a third-party digital signature processor/gateway server 360, a backend cloud-based server system 370, a patient history database 380, a pre-screening questionnaire database 385, an informed consent database 390, a patient image storage database 395, a calculated risk status & pre-anesthesia guidelines and requirements database 397, and an encryption and patient privacy compliance database 399.

In some embodiments, the web/mobile front-end server 350 is configured as a public-facing access point for connection to the website by the client-side computing devices. This is the initial starting point for patients and members of the pre-screening team to login with valid user credentials, such as username/password or other credentials. Thus, whenever a client-side computing device connects to the web/mobile front-end server 350, the user operating the particular client-side computing device either logs in or, if a new patient or new team member, registers for an account. This is true whether the user is interfacing with the web/mobile front-end server 350 via web browser to view the site as a conventional website such as when accessing via conventional computing device (e.g., desktop computer 310), or another form of presentation including, without limitation, a web app for the site, or a mobile app for the site, each of which may be supported by the particular client-side computing device operated by the user for the connection. For instance, a mobile app may provide the user interface when the user is operating a mobile device, such as the first mobile computing device 320, the second mobile computing device 330, or even the tablet computing device 340. Accordingly, when the user is a new user, the authentication firewall 354 of the platform 355 prevents access to the backend server system 370, and its combination of hardware resources, algorithms, tools, interfaces, implementations, and data resources. Thus, the new user may register a new account and provide information which is saved as a user account information for the new user. In some embodiments, the type of new user registration is managed by a permissions system that authorizes a combination of team member permissions that are different from the permissions authorized for individual patients. When registration is completed and all of the user profile information is provided, the web/mobile front-end server 350 stores the user account information in the user database 352, described next. In some embodiments, the web/mobile front-end server 350 is further configured to offload encryption processing (e.g., for processing of encrypted passwords, for instance) to a devoted encryption and patient privacy compliance system 399, by way of the authentication firewall 354.

In some embodiments, the user database 352 is configured to store each particular user account with a unique identifier (UID). In some embodiments, the UID distinguishes each separate user account from the other user accounts stored in the user database 352. Further delimiting the user accounts is a permissions system that automatically sets access permissions for each new user account according to the permissions to which the user is entitled. In some embodiments, the permissions system grants at least two types of permissions-a set of pre-screening team member permissions for new users who are on the pre-screening team and a different set of patient permissions for each patient who will be undergoing anesthesia in connection with a surgical procedure. In some embodiments, the UID of each particular user account comprises a passcode, a passphrase, a password, a unique numerical value, a hash-encrypted UID name value of the particular user's name, or a hash-encrypted UID all-data value of all information provided by the particular user (e.g., patient name, contact information, demographic information, etc.). In some embodiments, the hash-encrypted UID name value and the hash-encrypted UID all-data value is encrypted by the encryption and patient privacy compliance system 399 using a secure encryption scheme. In some embodiments, the secure encryption scheme comprises one of a symmetric-key encryption scheme and public-key encryption scheme. In some embodiments, the encryption scheme comprises Advanced Encryption Standard (AES) encryption. In some embodiments, the encryption scheme comprises Secure Hash Algorithm (SHA)

encryption. In some embodiments, the encryption scheme comprises another type of secure encryption scheme.

In some embodiments, the authentication firewall system 354 is configured to prevent unauthorized access to the backend cloud-based server system 370, through which access to the encryption and patient privacy compliance system 399 is provided, as well as access to other hardware resources, server tools, interfaces, etc. In this figure, the firewall is demonstrated by a "private cloud" item that partitions the front-end website from the backend server system 370 and all patient information stored in any of the databases. Thus, to access the backend server system 370 over the private cloud, the user would need to be successfully authenticated by the authentication firewall system 354. This may be done by the user providing login credentials which are then transmitted to the encryption and patient privacy compliance system 399 by the authentication firewall 354 and summarily authenticated by the encryption and patient privacy compliance system 399. If the encryption and patient privacy compliance system 399 determines that the login credentials are valid, then access over the private cloud is provided to the backend server system 370. In this way, all patient and other information being transmitted back and forth between client-side devices and the backend server system 370 are secure, encrypted, and only available to the valid users (based on their respective access permissions). Furthermore, with each user being assigned a unique UID, all patient data is linked to the UID. This prevents co-mingling of data from different patients and ensures full compliance with regulatory constraints and rules, such as those imposed by HIPAA or other regulatory frameworks. Notably, the authentication firewall system 354 of some embodiments implements the same encryption scheme as the encryption and patient privacy compliance system 399. In this way, the authentication firewall system 354 can do more than merely providing a firewall and transmission of encrypted data for authentication, storage, etc. In another variation (not shown in this figure), the authentication firewall system 354 is incorporated into the web/mobile front-end server 350 and, therefore, provides front-end server site authentication services.

In some embodiments, the third-party digital signature processor/gateway server 360 (or simply, the "digital signature server 360") is integrated into the platform 355 in the front-end and is configured to provide digital consent forms and process digital consent signatures provided by patients. In some embodiments, the digital signature server 360 comprises a third party digital signature server 360 deployed on and communicably connected to the platform 355. In some embodiments, the digital signature server 360 is a fully-integrated digital signature processing system that is incorporated into or communicably connected to the web/mobile front-end server 350 (and is, therefore, not truly an external, third party system). In some embodiments, the third-party digital signature server 360 is authenticated as a special user account with no access to the backend server system 370 but which is configured to receive—via a broker architecture supported by the cloud-based pre-anesthesia screening system 300—digital signatures provided by patients in the digital signature consent forms. In some embodiments, the digital signature broker architecture is configured to provide digital data representing each signature in messages between the backend server system 370 and the web/mobile front-end server 350 (and indirectly, the computing device operated by the patient who is providing the digital consent signature). In this way, the third-party digital signature server 360 is able to provide valid, accurate informed consent by each patient prior to anesthesia and surgery. In some embodiments, the backend server system 370 stores each digital signature in the informed consent database 390, after encryption on the digital signature is completed by the encryption and patient privacy compliance system 399.

In some embodiments, the backend server system 370 is the cloud-based anesthesia pre-screening server 370. In some embodiments, the cloud-based anesthesia pre-screening server 370 hosts the pre-anesthesia screening cloud application service, which is a program that implements algorithms, resources, and tools optimizing the utilization, storage, and retrieval of all patient information (including, without limitation, patient's answers to the questions in the pre-screening questionnaire, as well as digital consent signature) via the patient history data structure form that is designed to add patient answers/signature to pre-completed history of the patient and augment the information with relevant pathology information. Thus, while the pre-completed history of the patient would have been partially completed by a member of the pre-screening team in advance of surgery, there are many patients who are repeat patients getting a second, third, or fourth (no limit) surgery, and have simply provided updates to existing stored data linked to the patient's UID and securely stored in encrypted form. Also as shown in this figure, the cloud-based anesthesia pre-screening server 370 is communicably connected to the patient history database 380 which stores patient history data in encrypted form, and the pre-screening questionnaire database 385 which stores pre-screening questionnaires to present to patients as part of the anesthesia pre-screening process. Furthermore, the cloud-based anesthesia pre-screening server 370 is communicably connected to the informed consent database 390, the patient image database 395, the calculated risk status & pre-anesthesia guidelines and requirements database 397, and the encryption and patient privacy compliance database 399. In some embodiments, the cloud-based anesthesia pre-screening server 370 is also communicably connected, over the private cloud, to the authentication firewall 354, the web/mobile front-end server 350, and the digital signature server 360.

In some embodiments, the patient history database 380 is configured to store patient history data in the patient history data structure form for each patient as a singular archive of encrypted patient history data. In some embodiments, the patient history data structure provides a link field for storage of the UID corresponding uniquely to the patient. In this way, the patient history data (which is encrypted and stored in the compact, organized archive provided via the patient history data structure) is easily confirmed to relate to a particular user account in the user database 352 by linking of the UID.

In some embodiments, the pre-screening questionnaire database 385 is communicably connected to the cloud-based anesthesia pre-screening server 370 and is configured to store different versions of pre-screening questionnaires for different types of surgery, different types of anesthesia, and different considerations of different patients.

In some embodiments, the calculated risk status & pre-anesthesia guidelines and requirements database 397 is communicably connected to the cloud-based anesthesia pre-screening server 370 and is configured to store the calculated risk for each patient and is linked to the other patient data and imagery via the UID. In some embodiments, pre-anesthesia guidelines, recommendations, and requirements are provided to the patient based on the calculated risk. The pre-anesthesia guidelines, recommendations, and requirements are also stored in the calculated risk status & pre-anesthesia guidelines and requirements database 397.

In some embodiments, the informed consent database 390 is communicably connected to the cloud-based anesthesia pre-screening server 370 and is configured to store data representations of each patient signature provided digitally in the consent form.

In some embodiments, the patient image database 395 is communicably connected to the cloud-based anesthesia pre-screening server 370 and is configured to store all user-provided images (e.g., the imagery/photos of the patient's face and views for dentition and mallampati, etc.). In some embodiments, the patient image database 395 links the imagery stored for any particular patient to the other patient data via the UID for the particular patient. In some embodiments, the images stored in the patient image database 395 are encrypted by the encryption and patient privacy compliance system 399 prior to storage in the patient image database 395.

In some embodiments, the cloud-based pre-anesthesia screening system 300 and platform 355 provides a single database (not shown in this figure) that is communicably connected to the cloud-based anesthesia pre-screening server 370 and is configured to store all of the patient information, data, images, signatures, etc. (which as mentioned above are encrypted and stored in the user database 352, the patient history database 380, the informed consent database 390, the patient image storage database 395, the calculated risk status & pre-anesthesia guidelines and requirements database 397) in a single, consolidated database organized to uniquely identify to each patient in secure, encrypted form. In some embodiments, providing a single database for the cloud-based pre-anesthesia screening system 300 and platform 355 may involve deployment of multiple physical data storage devices that are logically configured as a single cluster database that is spread across multiple data storage (physical hardware) units. In some embodiments, a single, logically organized, cluster database (encompassing all the databases 380-397) may be part of a larger and more comprehensive data storage solution in which each separate logical cluster database is a portion of the larger and more comprehensive data storage (which could then accommodate storage of data for all pre-screening teams, all members of each pre-screening team, and other surgery/anesthesia databases) of the cloud-based pre-anesthesia screening system 300 and platform 355.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the terms "software", "program", "algorithm", "web app", "mobile app", etc., are meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 4:
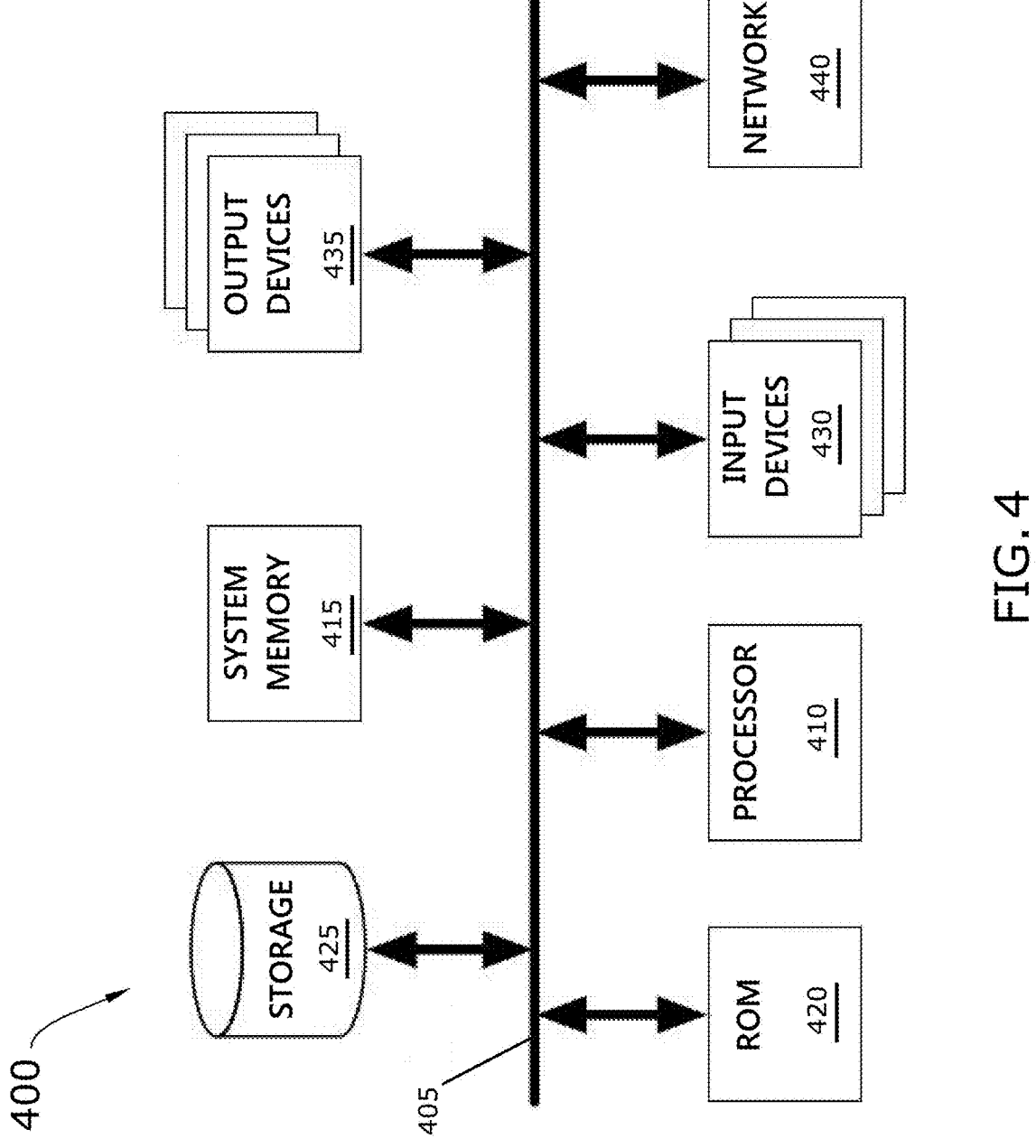
FIG. 4 conceptually illustrates an electronic system with which some embodiments of the invention are implemented.

By way of example, FIG. 4 conceptually illustrates an electronic system 400 with which some embodiments of the invention are implemented. The electronic system 400 may be a computer, a laptop, a server, a single board computer (SBC), a cloud server, a mobile device, a smart phone, a personal digital assistant (PDA), a tablet computing device, or any other sort of electronic device. Such an electronic system includes various types of computer readable media and interfaces for various other types of computer readable media. Electronic system 400 includes a bus 405, processing unit(s) 410, a system memory 415, a read-only memory 420, a permanent storage device 425, input devices 430, output devices 435, and a network 440.

The bus 405 collectively represents all system, peripheral, and chipset buses that communicatively connect the numerous internal devices of the electronic system 400. For instance, the bus 405 communicatively connects the processing unit(s) 410 with the read-only memory 420, the system memory 415, and the permanent storage device 425.

From these various memory units, the processing unit(s) 410 retrieves instructions to execute and data to process in order to execute the processes of the invention. The processing unit(s) may be a single processor or a multi-core processor in different embodiments.

The read-only-memory (ROM) 420 stores static data and instructions that are needed by the processing unit(s) 410 and other modules of the electronic system. The permanent storage device 425, on the other hand, is a read-and-write memory device. This device is a non-volatile memory unit that stores instructions and data even when the electronic system 400 is off. Some embodiments of the invention use a mass-storage device (such as a magnetic or optical disk and its corresponding disk drive) as the permanent storage device 425.

Other embodiments use a removable storage device (such as a floppy disk or a flash drive) as the permanent storage device 425. Like the permanent storage device 425, the system memory 415 is a read-and-write memory device. However, unlike storage device 425, the system memory 415 is a volatile read-and-write memory, such as a random access memory. The system memory 415 stores some of the instructions and data that the processor needs at runtime. In some embodiments, the invention's processes are stored in the system memory 415, the permanent storage device 425, and/or the read-only memory 420. For example, the various memory units include instructions for receiving answers to the questions presented to a patient in the questionnaire, encrypting the patient-provided answers, and storing the encrypted patient data in the patient history database 380. From these various memory units, the processing unit(s) 410 retrieves instructions to execute and data to process in order to execute the processes of some embodiments.

The bus 405 also connects to the input and output devices 430 and 435. The input devices enable the user to communicate information and select commands to the electronic system. The input devices 430 include alphanumeric keyboards, cameras for still images and/or video, microphones for audio input (enabling the patient to audibly answer the questions in the questionnaire), as well as pointing or cursor control devices. The output devices 435 display images and textual information based on the user-provided input (for example, the patient's calculated risk after processing is completed on the patient-provided answers to the questionnaire and other factors noted above). The output devices 435 include printers and display devices, such as liquid crystal displays (LCD) and organic light emitting diode (OLED) displays. Some embodiments include a touchscreen that functions as both an input and output device.

Finally, as shown in FIG. 4, bus 405 also couples electronic system 400 to a network 440 through a network adapter (not shown). In this manner, the computing device or electronic system 400 can be a part of a network of computers (such as a local area network ("LAN"), a wide area network ("WAN"), or an Intranet), or a network of networks (such as the Internet). Any or all components of electronic system 400 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes and logic flows may be performed by one or more programmable processors and by sets of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the anesthesia pre-screening system and platform can be embodied in other specific forms without departing from the spirit of the invention. For instance, FIGS. 1-2 conceptually illustrate processes in which the specific operations of these processes may not be performed in the exact order shown and described. Specific operations may not be performed in one continuous series of operations, and different specific operations may be performed in different embodiments. Furthermore, the processes could be implemented using several sub-processes, or as part of a larger macro process. Thus, one of ordinary skill in the art would understand that the invention is not to be limited by the foregoing illustrative details, but rather is to be defined by the appended claims.

We claim:

1. An anesthesia pre-screening system comprising:
a web/mobile front-end server configured to provide a patient-facing pre-anesthesia questionnaire user interface and to transmit, to a patient account, a digital message that includes a hyperlink address to the patient-facing pre-anesthesia questionnaire user interface;

an authentication firewall system configured to (i) authenticate user credentials and (ii) provide, based on successful authentication, access over a private cloud partition to backend services while preventing unauthorized access to the backend services;

a permissions system configured to authorize a first set of permissions for a pre-screening team member and a second set of permissions for a patient;

a backend cloud-based server system configured, upon access being provided by the authentication firewall system, to host a pre-anesthesia screening cloud application service that implements at least a portion of a digital anesthesia pre-screening process;

a user database configured to store user account information and, for each user account, a unique identifier (UID) that distinguishes the user account from other user accounts;

a pre-anesthesia questionnaire aggregation system configured to receive patient-provided questionnaire answers entered through the patient-facing pre-anesthesia questionnaire user interface;

a digital consent form and e-signature system configured to (i) visually output, via the web/mobile front-end server, a consent form including a consent signature field after the patient has answered a plurality of questions of the pre-anesthesia questionnaire, and (ii) receive a digital patient consent signature provided by the patient in the consent signature field;

a patient history database configured to store, for each patient, a patient history data structure that includes (i) a UID link field storing the UID which uniquely corresponds to the patient and (ii) patient history data for the patient, wherein the backend cloud-based server system is configured to automatically incorporate, in the patient history data structure, the patient-provided questionnaire answers and the digital patient consent signature as patient pre-screening data that augments the patient history data;

an HL7 data plug-in that is configured to analyze and input information from electronic health databases into the patient history data structure in compliance with HIPAA;

an image acquisition and incorporation unit that is configured to receive and store patient image data comprising one or more patient photos uploaded by the patient via the patient-facing pre-anesthesia questionnaire user interface, wherein the patient image data is linked to the patient history data structure by the UID;

a vitals data unit configured to receive and store medical data comprising preoperative vitals data and results of testing, wherein the medical data is linked to the patient history data structure by the UID;

an encryption and patient privacy compliance system configured to encrypt and securely store (i) the UID-linked patient history data structure and (ii) patient health data comprising the patient-provided questionnaire answers, the digital patient consent signature, the patient image data, and the medical data, such that patient health data is stored in association with the UID to prevent commingling and in compliance with HIPAA;

a surgical risk calculator configured to automatically calculate a surgical risk for the patient based on at least a portion of the patient health data linked by the UID;

a calculated risk status and pre-anesthesia guidelines and requirements database configured to store a calculated risk status for the patient and one or more pre-anesthesia guideline or requirement records linked to the UID;

an anesthesia departmental listing system configured to (i) generate—based on the patient history data structure, a type of surgery, and individual department guidelines—one or more pre-anesthesia indicators comprising recommended lab work, pre-screening testing, medical clearances required, and medications to stop, and (ii) provide the one or more pre-anesthesia indicators for review by an authenticated pre-screening team member; and an anesthesia discharge instruction unit that is configured to provide anesthesia discharge instructions customized for the patient based on at least the calculated risk status linked to the UID.

2. The anesthesia pre-screening system of claim 1, wherein the backend cloud-based server system is further configured to digitally transmit patient health data linked to the UID to an authenticated pre-screening team member only after the patient provides an affirmative consent to transmit the personal health information of the patient via a patient-facing consent control presented by the web/mobile front-end server.

3. The anesthesia pre-screening system of claim 1, wherein the authentication firewall system separates the web/mobile front-end server from the backend cloud-based server system such that access to the backend cloud-based server system is provided only upon successful authentication of login credentials using the encryption and patient privacy compliance system.

4. The anesthesia pre-screening system of claim 1, wherein the permissions system is configured to grant permissions for a pre-screening team member that are different from patient permissions, wherein the different permissions restrict access such that only a pre-screening team member account is authorized to access the calculated risk status stored in the calculated risk status and pre-anesthesia guidelines and requirements database.

5. The anesthesia pre-screening system of claim 1, further comprising an informed consent database, wherein the digital consent form and e-signature system comprises a digital signature gateway server configured to receive the digital patient consent signature and store an encrypted representation of the digital patient consent signature in the informed consent database.

6. The anesthesia pre-screening system of claim 1, wherein the patient image data comprises at least one of a patient face image, a dentition image, and a Mallampati view image uploaded via the patient-facing pre-anesthesia questionnaire user interface.

7. The anesthesia pre-screening system of claim 1, further comprising a patient image database, wherein the encryption and patient privacy compliance system is configured to encrypt patient image data prior to storage as UID-linked patient image records in the patient image database.

8. The anesthesia pre-screening system of claim 1, wherein the surgical risk calculator is configured to calculate surgical risk using one or more risk scoring frameworks comprising at least one of an NSQIP surgical risk calculator, a Revised Goldman Cardiac Risk framework, a peri-operative acute kidney injury risk model, a MELD score, or an APACHE score.

9. The anesthesia pre-screening system of claim 1, further comprising an audio-to-text subsystem configured to convert audio input into text, wherein the pre-anesthesia questionnaire aggregation system is configured to receive questionnaire answers comprising at least one of (i) text input, (ii) audio input captured by a microphone, and (iii) video input captured by a camera, and wherein the audio-to-text subsystem converts audio input into text for incorporation into the patient history data structure.

10. The anesthesia pre-screening system of claim 1, wherein the anesthesia departmental listing system is configured to highlight potential high-risk patients based on the calculated risk status stored in the calculated risk status and pre-anesthesia guidelines and requirements database.

\* \* \* \* \*